United States Patent
Delmas et al.

(10) Patent No.: US 11,319,506 B2
(45) Date of Patent: May 3, 2022

(54) USE OF A COMPOSITION CONTAINING 1,8-PARA-MENTHENETHIOL AND 3-MERCAPTOHEXYL ACETATE AS AN ODOR-MASKING AGENT

(71) Applicant: JAFER ENTERPRISES R&D SL, Granollers (ES)

(72) Inventors: Thomas Delmas, Antibes (FR); Antoine Gouteyron, Le Cannet (FR); Marion Perez, Villeneuve-Loubet (FR)

(73) Assignee: JAFER ENTERPRISES R&D SL, Granollers (ES)

( * ) Notice: Subject to any disclaimer, the term of this patent is extended or adjusted under 35 U.S.C. 154(b) by 37 days.

(21) Appl. No.: 16/494,427

(22) PCT Filed: Mar. 15, 2018

(86) PCT No.: PCT/EP2018/056519
§ 371 (c)(1),
(2) Date: Sep. 16, 2019

(87) PCT Pub. No.: WO2018/167206
PCT Pub. Date: Sep. 20, 2018

(65) Prior Publication Data
US 2020/0299613 A1    Sep. 24, 2020

(30) Foreign Application Priority Data

Mar. 17, 2017   (FR) ...................... 1752175

(51) Int. Cl.
| | | |
|---|---|---|
| *C11B 9/00* | (2006.01) |
| *A61K 8/31* | (2006.01) |
| *A61K 8/46* | (2006.01) |
| *A61K 8/9789* | (2017.01) |
| *A61K 8/34* | (2006.01) |
| *A61K 8/37* | (2006.01) |
| *A61L 9/03* | (2006.01) |
| *A61L 9/14* | (2006.01) |
| *A61L 15/46* | (2006.01) |
| *A61Q 5/02* | (2006.01) |
| *A61Q 15/00* | (2006.01) |
| *A61Q 19/10* | (2006.01) |
| *C11D 3/00* | (2006.01) |
| *D06M 13/00* | (2006.01) |
| *B01D 11/02* | (2006.01) |
| *B01D 46/00* | (2022.01) |
| *D06M 101/06* | (2006.01) |

(52) U.S. Cl.
CPC .............. *C11B 9/0011* (2013.01); *A61K 8/31* (2013.01); *A61K 8/34* (2013.01); *A61K 8/37* (2013.01); *A61K 8/46* (2013.01); *A61K 8/9789* (2017.08); *A61L 9/037* (2013.01); *A61L 9/14* (2013.01); *A61L 15/46* (2013.01); *A61Q 5/02* (2013.01); *A61Q 15/00* (2013.01); *A61Q 19/10* (2013.01); *C11B 9/0003* (2013.01); *C11B 9/0007* (2013.01); *C11B 9/0015* (2013.01); *C11B 9/0019* (2013.01); *C11B 9/0034* (2013.01); *C11D 3/0068* (2013.01); *D06M 13/005* (2013.01); *B01D 11/0203* (2013.01); *B01D 46/0038* (2013.01); *D06M 2101/06* (2013.01)

(58) Field of Classification Search
CPC .... A61K 2800/5922; A61K 8/31; A61K 8/34; A61K 8/37; A61K 8/46; A61K 8/9789; A61Q 13/00; A61Q 15/00; A61Q 19/10; A61Q 5/02; C11B 9/0003; C11B 9/0007; C11B 9/0011; C11B 9/0015; C11B 9/0019; C11B 9/0034
USPC .......................................................... 424/65
See application file for complete search history.

(56) References Cited

U.S. PATENT DOCUMENTS

| | | | |
|---|---|---|---|
| 2015/0030744 A1 | 1/2015 | Lombardo et al. | |
| 2016/0165899 A1* | 6/2016 | Bissinger | A01N 37/36 424/745 |
| 2016/0354304 A1 | 12/2016 | Anderson | |

FOREIGN PATENT DOCUMENTS

| | | | |
|---|---|---|---|
| WO | WO 2016/138186 | 9/2016 | |
| WO | WO-2016138186 A1 * | 9/2016 | ............... A61L 9/01 |

OTHER PUBLICATIONS

Jabalpurwala et al. Food Chemistry 120 (2010) 296-303.*
Singh, T. P. et al. "Phytochemical and pharmacological profile of *Zanthoxylum armatum* DC.—An overview" *Indian Journal of Natural Products and Resources*, Sep. 2011, pp. 275-285, vol. 2, No. 3.
Written Opinion in International Application No. PCT/EP2018/056519, dated May 9, 2018, pp. 1-6.

* cited by examiner

*Primary Examiner* — Ali Soroush
*Assistant Examiner* — Courtney A Brown
(74) *Attorney, Agent, or Firm* — Saliwanchik, Lloyd & Eisenschenk

(57) ABSTRACT

The present invention relates to the use of a composition containing 1,8-para-menthenethiol and 3-mercaptohexyl acetate, such as a plant extract and in particular an extract of timur (*Zanthoxylum armatum*), as odor-masking agent. It also relates to a deodorizing product in the form of an aerosol, candle, or electrical or wick fragrance diffuser, containing this composition.

9 Claims, No Drawings

USE OF A COMPOSITION CONTAINING 1,8-PARA-MENTHENETHIOL AND 3-MERCAPTOHEXYL ACETATE AS AN ODOR-MASKING AGENT

CROSS-REFERENCE TO RELATED APPLICATION

This application is the U.S. national stage application of International Patent Application No. PCT/EP2018/056519, filed Mar. 15, 2018.

SUBJECT OF THE INVENTION

The present invention relates to the use of a composition containing 1,8-para-menthenethiol and 3-mercaptohexyl acetate, such as a plant extract and in particular an extract of timur (*Zanthoxylum armatum*), as odor-masking agent. It also relates to a deodorizing product in the form of an aerosol, candle, or electrical or wick fragrance diffuser, containing this composition.

BACKGROUND OF THE INVENTION

Numerous products capable of reducing or masking unpleasant odors are commercially available and have been described in the literature. These deodorizing products act either physically, by trapping the molecules responsible for the unpleasant odors in filters having a suitable porosity and specific surface area, especially cyclodextrins, or chemically, by chemically modifying these molecules, or sensorially, by masking the unpleasant odors using fragrances which make it possible to reduce the perception of unpleasant odors. Among the latter, the majority are in the form of aerosols using propellant gases based on hydrocarbons, which enable a very rapid diffusion of a fragrance containing a mixture of aldehydes. While these compounds are capable of reducing the impact of unpleasant odors, they are subject to oxidation and, after spraying onto fabrics, cause pronounced yellowing when exposed to light.

Research has therefore been undertaken to identify other compounds capable of effectively masking unpleasant odors.

In this context, it is known that 1,8-para-menthenethiol, or thioterpineol, can be used as an odor-masking agent (WO 2016/058710). However, it became apparent to the applicant that the effectiveness thereof was not always sufficient against some odors and, after significant amounts of research, it has been demonstrated that the effectiveness of this compound could be reinforced by combining it with 3-mercaptohexyl acetate. Of course, the latter is known as an odorizing molecule responsible, in particular, for the exotic fruit aromas of some fruit, but it could not have been predicted that it would make it possible to improve the effectiveness of thioterpineol, in the sense that it is well known that the combination of odorizing molecules may have an effect which is antagonistic to that obtained when these molecules are used individually.

The applicant has moreover demonstrated that the abovementioned combination of molecules was present in some plant extracts and in particular in a volatile composition extracted from *Zanthoxylum armatum*, which was hitherto unknown (see in particular T. P. Singh et al., *Indian Journal of Natural Products and Resources*, 30 Sep. 2011, pages 275-285). The applicant thus envisioned using these extracts as odor-masking agents in different deodorizing products.

The species *Zanthoxylum armatum* or *planispinum* belongs to the family of the Rutaceae. It is a plant which grows in Asia, and in particular in Nepal, the berries of which constitute timur pepper. It has been suggested to use timur extracts (without specifying the composition thereof or the method for extracting them) as agent for generating tingling in flavoring compositions (US 2015/030744) or fragrancing compositions (WO 2016/138186). A deodorizing and antiseptic effect of flavonoid-rich timur extracts has also been mentioned (see above, T. P. Singh et al). This type of extract is conventionally obtained by aqueous-alcoholic extraction. The essential oil extracted from these berries is known to treat numerous disorders. It has also been envisioned to use the supercritical $CO_2$ extraction product of timur berries in products for the lips (US 2016/354304). However, to the applicant's knowledge, as yet it has never been suggested that this type of extract could have a benefit as an odor-masking agent.

SUMMARY OF THE INVENTION

Thus, a subject of the invention is the use of a composition containing 1,8-para-menthenethiol and 3-mercaptohexyl acetate as an odor-masking agent.

Another subject of the invention is a deodorizing product in the form of an aerosol, candle, or electrical or wick fragrance diffuser, containing the abovementioned composition.

DETAILED DESCRIPTION

The composition used according to the invention comprises a specific thiol and a specific ester, namely 1,8-para-menthenethiol and 3-mercaptohexyl acetate. It also advantageously contains at least one constituent chosen from: linalool, limonene, myrcene, methyl cinnamate, 3-phellandrene, 4-mercapto-4-methylpentan-2-one, 3-mercaptohexanol and a mixture thereof, preferably a mixture of all the above-mentioned constituents. According to one embodiment of the invention, the composition contains from 5 to 99% of volatile and semi-volatile products which contain from 50 to 95% by weight of a combination of linalool, limonene, myrcene and methyl cinnamate. "Volatile product" is intended to mean a product having a vapor pressure of less than 13.34 Pa (0.1 mm Hg) at 20° C. or a boiling point of less than 216° C. "Semi-volatile product" is intended to mean a product having a boiling point of between 216 and 350° C.

All the above-mentioned constituents may be derived from one or more plant extracts containing them in the natural state. According to a preferred embodiment of the invention, the composition is therefore a plant extract or a mixture of plant extracts. According to another embodiment, the constituents of the composition according to the invention may each be obtained independently by chemical synthesis or from a plant extract, then mixed to form said composition.

When the composition used according to the invention is a plant extract, it is preferable for it to be an extract of timur (*Zanthoxylum armatum*), which can be obtained from any part of timur and in particular the leaves thereof, the trunk thereof, the fruit (berries) thereof or the pericarp of said berries. More preferentially, use is made of an extract of timur berries.

In a preferred embodiment of the invention, the timur berries may be dried and/or ground by any means prior to the extraction thereof, especially by cryogenic grinding. Indeed, it has been observed that the ground berries had a better balance between their different olfactory notes, due in particular to a modification of the monoterpenes/linalool ratio. The mean particle size distribution (D50) of the ground berries may especially be between 200 and 600 μm, as measured by screening.

Since the compounds used according to the invention are also present separately in plant extracts other than those derived from timur, as a variant, the composition according to the invention may consist of a mixture of plant extracts, for example a mixture of an extract of black grape, of passion fruit or of hops (containing 3-mercaptohexyl acetate) and of grapefruit, of trifoliate orange (*Poncirus trifoliata*) or of orange (containing 1,8-para-menthenethiol).

The extraction of the plant parts chosen to obtain the plant extract(s) used according to the invention may be carried out by hydrodistillation or preferentially using supercritical $CO_2$. In the case of timur, supercritical $CO_2$ extraction makes it possible to obtain an extract having a fragrance which is more potent, more long-lasting and less rich in aldehydes than extraction by hydrodistillation. These characteristics could be associated with the greater richness in fatty acids and in esters of the volatile fraction obtained in this way. The conditions for carrying out these processes will be able to be readily determined by those skilled in the art. Thus, the extraction with supercritical $CO_2$ may for example be carried out at a temperature of 30 to 60° C., for example of 35 to 50° C., under a pressure of 50 to 150 bar, for example of 80 to 100 bar.

The plant extract obtained may optionally be dried by any means, generally to a moisture content of 0 to 10% by weight, before being used according to the invention.

The presence of 1,8-para-menthenethiol and 3-mercaptohexyl acetate in the plant extract may be confirmed in particular by modification of these thiols with 4,4'-dithiodipyridine or N-phenylmaleimide, respectively, then analysis by ultra-high-performance liquid chromatography (UHPLC) coupled with a qualitative and quantitative analysis by mass spectrometry (QqQ MS).

The composition according to the invention may be used to mask any type of odors, especially chosen from indole odors, amine odors (in particular ammonia and skatole), thiol odors (especially dimethyl trisulfide or thiophenol) or acid odors (especially isovaleric acid). It may also serve to mask these odors in any type of environment in which it is applied, especially on the body, or in premises for domestic, commercial or industrial use. As a variant, this composition may be combined with products which themselves have an unpleasant odor or which are liable to generate unpleasant odors during their use. The composition according to the invention may thus be added to a deodorizing product; a detergent product such as laundry detergent or a household cleaner (especially a product for cleaning toilets or dishes); a bodily hygiene product such as a deodorant, an antiperspirant, a soap or a shampoo; or a hair dyeing product, without this list being limiting. In a preferred embodiment of the invention, this composition is incorporated into a deodorizing product. The invention therefore also relates to a deodorizing product in the form of an aerosol, candle, or electrical or wick fragrance diffuser, containing a composition containing 1,8-para-menthenethiol and 3-mercaptohexyl acetate, as defined above. This product is in particular intended to be used as interiors and/or textiles deodorizer.

Aside from the abovementioned composition, the product incorporating same may comprise different constituents making it possible in particular for this product to be in a form suited to its use, especially in liquid, gel, mousse, or cream form or else in solid form. These constituents may for example comprise solvents such as water and/or hydrocarbon-based or silicone polar or nonpolar organic solvents; surfactants; aqueous phase gelling agents; oily phase thickeners; preservatives; antioxidants; chelating agents; polyols; odor absorbers such as zeolites, cyclodextrins, silica, aluminosilicates or activated carbon; UV absorbers; antimicrobial agents; fragrances such as essential oils; pigments; and dyes, without this list being limiting, as long as these constituents do not adversely affect the deodorizing properties of the composition according to the invention. The composition according to the invention may moreover be conveyed in microspheres, nanocapsules, microcapsules, liposomes or any other vector enabling the incorporation thereof in the abovementioned product and optionally the sustained release of its constituents. The incorporation of the composition according to the invention into the abovementioned products may especially be carried out by mixing their constituents.

The composition according to the invention represents for example from 0.01 to 20% by weight, preferably from 0.05 to 5% by weight relative to the weight of the product into which it is incorporated.

According to one embodiment of the invention, the composition may be impregnated on a nonwoven product, especially a wipe. In yet another embodiment, the composition according to the invention may be incorporated into an absorbent hygiene product such as a baby's diaper and in particular into the absorbent core and/or at least one of the nonwoven layers and/or the plastic films constituting the upper and lower layers of the absorbent product and/or within elastic.

EXAMPLES

The invention will be better understood in light of the following examples which are given purely by way of illustration and the aim of which is not to limit the scope of the invention, defined by the appended claims.

Example 1: Preparation of a Composition According to the Invention

An unpleasant odor reducer (UOR) was prepared, consisting of an extract of timur berries obtained by extraction using supercritical $CO_2$.

For this purpose, timur berries are first cryogenically ground by treating them with a stream of nitrogen at −196° C. before passing them into a cutting mill (model SM100® from RETSCH). A homogeneous powder is thus obtained, the particle size distribution of which is predominantly in the range from 200 to 600 µm. This powder is placed in a stainless steel cartridge and this cartridge is placed in a supercritical fluid extractor (SFE5® by SEPAREX). The extraction is carried out using supercritical $CO_2$ at a solvent/raw material ratio of approximately 4. The pressure within the extractor is set at 80-120 bar and the temperature at 35-50° C.

The analysis of the extract obtained shows it contains 1,8-para-menthenethiol and 3-mercaptohexyl acetate.

Example 2: Deodorizing Effect of a Composition Based on *Zanthoxylum armatum*

Example 2A: Test on Cotton

A series of tests were carried out with the aim of determining the odor-masking effect of the UOR of example 1 in relation to various molecules responsible for unpleasant odors (UO). For this purpose, one or two squares of cotton of 1 $cm^2$, impregnated with different concentrations of UO, were placed in sealed 15 ml bottles in the presence of two different concentrations of the UOR. The olfactory intensity of the unpleasant odor was evaluated by a panel of two experts 2 h 30 after having sealed the bottle and was compared to a control consisting of an identical bottle not comprising UOR.

The results obtained are grouped together in table 1 below, where the percentage reduction in unpleasant odor corresponds to the fraction of the unpleasant odor of the control still present in the bottle tested, and "UOR×A" denotes an amount of UOR which is A times greater than that of the UO.

TABLE 1

| UO | Number of cottons | Reduction in unpleasant odor (%) of the $CO_2$ timur | | |
|---|---|---|---|---|
| | | UOR × 40 | UOR × 100 | UOR × 200 |
| Ammonia | 2 | 100 | 100 | 100 |
| Isovaleric acid | 1 | 100 | 100 | 100 |
| Thiophenol | 1 | 100 | 100 | 100 |

The extract of timur according to the invention is therefore highly effective against the unpleasant odors tested.

Example 2B: Test Under Real Conditions

This effect was confirmed on a larger scale. For this purpose, a model solution of UO was sprayed into a neutral standardized room of 25 $m^3$, the temperature of which was set to 22±2° C. The solution used contained a mixture of 5 to 100 ppm of skatole, 5 to 100 ppm of dimethyl trisulfide, 5 to 100 ppm of thiophenol, 80 to 4000 ppm of ammonia and 30 to 600 ppm of isovaleric acid. Ten sprays were carried out. A candle formulated using the UOR of example 1 was then lit. It contained from 1 to 10% by weight of extract of timur and from 90 to 99% by weight of a pre-formulated mixture of beeswax (33%) and stearic acid (66%). The olfactory intensity over time of the UO was evaluated by a panel of two experts and five laypeople, with a view to determining the time after which the UO was no longer perceptible. A comparison was made under the same conditions but without a candle, and with a candle devoid of UOR according to the invention (to evaluate the effect of burning).

The results obtained are grouped together in table 2 below.

TABLE 2

| Candle tested | — | Neutral | 1% UOR | 3% UOR | 5% UOR | 10% UOR |
|---|---|---|---|---|---|---|
| Time for elimination of UO | 55 min | 40 min | 30 min | 25 min | 20 min | 15 min |

These results confirm the effectiveness of the composition according to the invention.

Example 3: Demonstration of an Effect of Promoting Reduction in Unpleasant Odors Example 2A was repeated, replacing the extract of timur used with a solution of 1,8-para-menthenethiol (PMT), alone or combined with 3-mercaptohexyl acetate (3MHA) in a weight ratio of 50/50 to retain a molar ratio [UOR]/[UO] of 0.2. This solution contained 0.025% of the 3MHA/PMT mixture and 99.975% of ethanol.

The results obtained are grouped together in table 3 below.

TABLE 3

| | Reduction in unpleasant odor (%) | | | |
|---|---|---|---|---|
| UO | Ammonia | Isovaleric acid | Thiophenol | Skatole |
| PMT | 0 | 40 | 100 | 100 |
| PMT + 3MHA (50/50) | 100 | 100 | 100 | 100 |
| 3MHA | 80 | 100 | 60 | 100 |

This test demonstrates that 3MHA has an effect of promoting reduction in unpleasant odors due to the isovaleric acid, and that a synergistic effect between 3MHA and PMT is even obtained in the case of ammonia. In addition, the 3MHA does not negatively affect the effect of reduction in the other unpleasant odors obtained with the PMT alone.

Example 4: Products Incorporating the Composition According to the Invention

The following formulations were prepared in a manner conventional to those skilled in the art, by mixing the ingredients below in the proportions by weight indicated.

| Ingredient | Formula 4.1.1 | Formula 4.1.2 | General case |
|---|---|---|---|
| Deionized water | Q.s. 100% | Q.s. 100% | Q.s. 100% |
| Polyethyleneimine | 0.0650% | 0.0650% | 0-1% |
| Diethylene glycol | 0.175% | 0.175% | 0-0.2% |
| Citric acid | 0.05% | 0.05% | 0-0.2% |
| 1,2-Benzisothiazolin-3-one | 0.003% | 0.003% | 0-0.01 |
| Ethanol | 3% | 3% | 0-5% |
| Sodium hydroxide | 0.003% | 0.003% | 0.001-0.01% |
| Fragrance | 0% | 0.4% | 0-2% |
| Extract of timur according to example 1 | 0.05% | 1% | 0.05-20% |

Example 4.1: Interiors and Textiles Deodorizers

Example 4.2: Deodorizing Aerosol

| Ingredient | Example | General case |
|---|---|---|
| Deionized water | Q.s. 100% | Q.s. 100% |
| Polyacrylic acid | 0.195% | 0-0.4% |
| Sodium citrate | 0.05% | 0-0.2% |
| Citric acid | 0.1% | 0-0.2% |
| Sodium lauryl sulfate | 0.145% | 0-0.2% |
| Ethanol | 5% | 0.1-10% |
| Sodium hydroxide | 0.075% | 0-0.1% |
| Organosilicone | 0.2% | 0-0.2% |
| PEG 60 | 1.4% | 0-2% |
| Fragrance | 1.2% | 0-1.5% |
| Extract of timur according to example 1 | 4% | 0.05-20% |

Example 4.3: Deodorant

| Ingredient | |
|---|---|
| Dipropylene glycol | 20-50% |
| Propylene glycol | 15-25% |
| Tripropylene glycol | 0-25% |
| Glycerol | 0-10% |
| PEG-8 | 0-20% |
| Water | 0-q.s. |
| Propylene glycol myristyl ether | 0-2% |
| Ethanol | Q.s. 100% |
| Sodium stearate | 5-6% |
| EDTA | 0.05-0.5% |
| Fragrance | 0-1.5% |
| Extract of timur according to example 1 | 0.05-5% |

Example 4.4: Candles

| Ingredient | Formula 4.4.1 | Formula 4.4.2 |
|---|---|---|
| Type of candle | Pillar candle | Jar |
| Paraffin wax, type 6003 | 5-50% | — |
| Stearic acid | 5-50% | — |
| Polymer (Vybar ®) | 5-50% | — |
| Alphawax ® Jarisma 1218 | — | 5-50% |
| Alphawax ® LA0186-T02 | — | 5-50% |
| White beeswax | — | 5-50% |
| Candelilla wax | — | 5-50% |
| Fragrance | 0-5% | 0-5% |
| Extract of timur according to example 1 | 0.05-20% | 0.05-20% |
| Total | 100% | 100% |

Example 4.5: Wax Melt

| Ingredient | |
|---|---|
| Caprylic/capric triglycerides | 5-15% |
| Soybean oil | 5-15% |
| Hydrogenated polyisobutene | 5-15% |
| Lanolin | 5-15% |
| Beeswax | 5-15% |
| Polyethylene 400 | 5-15% |
| Microcrystalline wax | 5-15% |
| Alpha-tocopherol | 0.05-0.2% |
| Fragrance | 0-1.5% |
| Extract of timur according to example 1 | 0.05-3% |
| Total | 100% |

Example 4.6: Composition for Wick Diffuser

| Ingredient | |
|---|---|
| Ethanol | 60-80% |
| Deionized water | 0.05-5% |
| Fragrance | 0-20% |
| Extract of timur according to example 1 | 0.05-20% |
| Total | 100% |

Example 4.7: Composition for Electric Diffuser

| Ingredient | |
|---|---|
| Isopropyl myristate | 60-80% |
| Deionized water | 0.05-5% |
| Fragrance | 0-20% |
| Extract of timur according to example 1 | 0.05-20% |
| Total | 100% |

Example 4.8: Hair Dyeing Composition

| Ingredient | |
|---|---|
| Hydrogen peroxide | 0.2-0.7% |
| Peracetic acid | 0.5-2% |
| 1-paraphenylenediamine | 0.1-0.5% |
| Basic Red 76 dye | 0-0.1% |
| EDTA | 0.05-0.2% |
| Ceteareth-25 | 0.5-3% |
| Cocamidopropyl betaine | 0.5-3% |
| Cetyl alcohol | 1-5% |
| Stearyl alcohol | 1-5% |
| Sodium sulfite | 0.05-0.2% |
| Water | Q.s. 100% |
| Extract of timur according to example 1 | 0.01-2% |

The formulations 4.1 to 4.8, used under standard conditions, have the advantage of masking the odors originating from the products themselves (case of aqueous ammonia for example 4.8) or else the odors originating from the surroundings (case of diffusers or candles) or else odors present after application (case of the deodorant 4.3).

The invention claimed is:

1. A method of masking odor comprising applying a composition containing 1,8-para-menthenethiol and 3-mercaptohexyl acetate to a body-textile or environment to mask an odor.

2. The method of claim 1, wherein said composition is applied to the environment or a premises in the form of an aerosol, candle, or electrical or wick fragrance diffuser.

3. The method of claim 1, wherein said composition further contains at least one constituent selected from the group consisting of: linalool, limonene, myrcene, methyl cinnamate, β-phellandrene, 4-mercapto-4-methylpentan-2-one, 3-mercaptohexanol and a mixture thereof.

4. The method of claim 1, wherein said composition further contains a mixture of linalool, limonene, myrcene, methyl cinnamate, β-phellandrene, 4-mercapto-4-methylpentan-2-one, and 3-mercaptohexanol.

5. The method of claim 1, wherein said composition is a plant extract or a mixture of plant extracts.

6. The method of claim 5, wherein said plant extract is obtained by extraction using supercritical $CO_2$ or by hydro-distillation.

7. The method of claim 5, wherein the plant extract is an extract of timur (*Zanthoxylum armatum*).

8. The method of claim 7, wherein timur berries are ground before extraction.

9. The method of claim 1, wherein said odors are selected from the group consisting of: indole, amine, thiol and acid odors.

* * * * *

UNITED STATES PATENT AND TRADEMARK OFFICE
CERTIFICATE OF CORRECTION

PATENT NO. : 11,319,506 B2
APPLICATION NO. : 16/494427
DATED : May 3, 2022
INVENTOR(S) : Thomas Delmas, Antoine Gouteyron and Marion Perez It is certified that error appears in the above-identified patent and that said Letters Patent is hereby corrected as shown below:

On the Title Page

Please replace the title page, with the attached title page, showing the corrected number of claims.

In the Specification

Column 2,
Lines 44-45, "3-phellandrene" should read --β-phellandrene--.

In the Claims

Column 10,
Line 7, "to a body-textile" should read --to a body, textile--.
Lines 32-33, "none" should read --10. The method of claim 1, wherein said composition is applied to a body in the form of a deodorant, an antiperspirant, a soap, a shampoo, or a hair dyeing product.--.

Signed and Sealed this
Twenty-third Day of January, 2024

*Katherine Kelly Vidal*

Katherine Kelly Vidal
*Director of the United States Patent and Trademark Office*

# CERTIFICATE OF CORRECTION (continued)

(12) United States Patent
Delmas et al.

(10) Patent No.: US 11,319,506 B2
(45) Date of Patent: May 3, 2022

(54) USE OF A COMPOSITION CONTAINING 1,8-PARA-MENTHENETHIOL AND 3-MERCAPTOHEXYL ACETATE AS AN ODOR-MASKING AGENT

(71) Applicant: JAFER ENTERPRISES R&D SL, Granollers (ES)

(72) Inventors: Thomas Delmas, Antibes (FR); Antoine Gouteyron, Le Cannet (FR); Marion Perez, Villeneuve-Loubet (FR)

(73) Assignee: JAFER ENTERPRISES R&D SL, Granollers (ES)

( * ) Notice: Subject to any disclaimer, the term of this patent is extended or adjusted under 35 U.S.C. 154(b) by 37 days.

(21) Appl. No.: 16/494,427

(22) PCT Filed: Mar. 15, 2018

(86) PCT No.: PCT/EP2018/056519
§ 371 (c)(1),
(2) Date: Sep. 16, 2019

(87) PCT Pub. No.: WO2018/167206
PCT Pub. Date: Sep. 20, 2018

(65) Prior Publication Data
US 2020/0299613 A1   Sep. 24, 2020

(30) Foreign Application Priority Data
Mar. 17, 2017 (FR) .................. 1752175

(51) Int. Cl.
| | |
|---|---|
| *C11B 9/00* | (2006.01) |
| *A61K 8/31* | (2006.01) |
| *A61K 8/46* | (2006.01) |
| *A61K 8/9789* | (2017.01) |
| *A61K 8/34* | (2006.01) |
| *A61K 8/37* | (2006.01) |
| *A61L 9/03* | (2006.01) |
| *A61L 9/14* | (2006.01) |
| *A61L 15/46* | (2006.01) |
| *A61Q 5/02* | (2006.01) |
| *A61Q 15/00* | (2006.01) |
| *A61Q 19/10* | (2006.01) |
| *C11D 3/00* | (2006.01) |
| *D06M 13/00* | (2006.01) |
| *B01D 11/02* | (2006.01) |
| *B01D 46/00* | (2022.01) |
| *D06M 101/06* | (2006.01) |

(52) U.S. Cl.
CPC ............ *C11B 9/0011* (2013.01); *A61K 8/31* (2013.01); *A61K 8/34* (2013.01); *A61K 8/37* (2013.01); *A61K 8/46* (2013.01); *A61K 8/9789* (2017.08); *A61L 9/037* (2013.01); *A61L 9/14* (2013.01); *A61L 15/46* (2013.01); *A61Q 5/02* (2013.01); *A61Q 15/00* (2013.01); *A61Q 19/10* (2013.01); *C11B 9/0003* (2013.01); *C11B 9/0007* (2013.01); *C11B 9/0015* (2013.01); *C11B 9/0019* (2013.01); *C11B 9/0034* (2013.01); *C11D 3/0068* (2013.01); *D06M 13/005* (2013.01); *B01D 11/0203* (2013.01); *B01D 46/0038* (2013.01); *D06M 2101/06* (2013.01)

(58) Field of Classification Search
CPC .... A61K 2800/5922; A61K 8/31; A61K 8/34; A61K 8/37; A61K 8/46; A61K 8/9789; A61Q 13/00; A61Q 15/00; A61Q 19/10; A61Q 5/02; C11B 9/0003; C11B 9/0007; C11B 9/0011; C11B 9/0015; C11B 9/0019; C11B 9/0034
USPC .................................................. 424/65
See application file for complete search history.

(56) References Cited

U.S. PATENT DOCUMENTS

| | | |
|---|---|---|
| 2015/0030744 A1 | 1/2015 | Lombardo et al. |
| 2016/0165899 A1* | 6/2016 | Bissinger ............ A01N 37/36 424/745 |
| 2016/0354304 A1 | 12/2016 | Anderson |

FOREIGN PATENT DOCUMENTS

| | | | |
|---|---|---|---|
| WO | WO 2016/138186 | 9/2016 | |
| WO | WO-2016138186 A1 * | 9/2016 | ............ A61L 9/01 |

OTHER PUBLICATIONS

Jabalpurwala et al. Food Chemistry 120 (2010) 296-303.*
Singh, T. P. et al. "Phytochemical and pharmacological profile of *Zanthoxylum armatum* DC.—An overview" *Indian Journal of Natural Products and Resources*, Sep. 2011, pp. 275-285, vol. 2, No. 3.
Written Opinion in International Application No. PCT/EP2018/056519, dated May 9, 2018, pp. 1-6.

* cited by examiner

*Primary Examiner* — Ali Soroush
*Assistant Examiner* — Courtney A Brown
(74) *Attorney, Agent, or Firm* — Saliwanchik, Lloyd & Eisenschenk

(57) ABSTRACT

The present invention relates to the use of a composition containing 1,8-para-menthenethiol and 3-mercaptohexyl acetate, such as a plant extract and in particular an extract of timur (*Zanthoxylum armatum*), as odor-masking agent. It also relates to a deodorizing product in the form of an aerosol, candle, or electrical or wick fragrance diffuser, containing this composition.

10 Claims, No Drawings